United States Patent [19]
Jungmann-Campello et al.

[11] Patent Number: 5,747,333
[45] Date of Patent: May 5, 1998

[54] CULTURE OF MICRO-ORGANISMS

[75] Inventors: Diana DeMello Jungmann-Campello, Manchester; Uri Friedlaender, London, both of England

[73] Assignee: Jencons (Scientific) Limited, Bedfordshire, England

[21] Appl. No.: 764,056

[22] Filed: Dec. 12, 1996

[51] Int. Cl.$^6$ .................................................. C12M 3/00
[52] U.S. Cl. ........................... 435/283.1; 435/288.3; 435/305.1; 435/809; 422/104
[58] Field of Search ............................ 435/283.1, 288.3, 435/305.1, 305.3, 305.4, 809; 422/104

[56] References Cited

U.S. PATENT DOCUMENTS

| | | | |
|---|---|---|---|
| 3,203,870 | 8/1965 | Andelin | 435/305.4 |
| 3,630,849 | 12/1971 | Land et al. | 435/305.4 |
| 4,728,607 | 3/1988 | Dorn et al. | 435/305.4 |

*Primary Examiner*—David A. Redding
*Attorney, Agent, or Firm*—Lee, Mann, Smith, McWilliams, Sweeney & Ohlson

[57] ABSTRACT

Disclosed is a Petri dish support device comprising two opposed portions, and a space defined between said opposed portions capable of receiving a sheet of material having marked thereon a matrix, the support being adapted to secure a Petri dish above the marked matrix, the matrix being visible through the base of the Petri dish.

20 Claims, 3 Drawing Sheets

CULTURE OF MICRO-ORGANISMS

FIELD OF THE INVENTION

This invention relates to a device for use in the preparation of micro-organism cultures.

BACKGROUND OF THE INVENTION

It is well-known to culture micro-organisms (e.g. bacteria, yeast and fungi) on solid, translucent media such as agar. Such cultures are often useful, for example, in the fields of molecular biology and genetics. In particular, it is often desired to screen a plurality of discrete micro-organism colonies for the presence of a particular characteristic (e.g. a genotypic feature such as the ability to hybridise with a particular nucleic acid probe, or a phenotypic characteristic such as the ability to grow in the presence of a particular substance or combination of substances).

In this regard, it is useful to grow micro-organisms on the surface of a solid medium (typically in a Petri dish) in a particular matrix. It is known, for example, to mark a grid pattern of numbered squares on a piece of paper and to position the piece of paper in the up-turned lid of a spare Petri dish. The base of a Petri dish may then be placed inside the up-turned lid (the lid being of greater diameter than the base), with the paper grid pattern being visible through the translucent growth medium and the transparent plastics material of the Petri dish. Reference marks are then made on both the up-turned lid and the base of the Petri dish, indicating the spatial relationship of the up-turned lid and the base of the Petri dish, such that the lid and base may subsequently be re-positioned in substantially the same spatial relationship. Next, the growth medium in the base of the Petri dish is inoculated with small inocula of the micro-organism(s) of interest in a pattern according to the paper grid visible through the growth medium. The Petri dish is then removed from the up-turned Petri dish lid, and may then be incubated under appropriate conditions to cause the micro-organisms to grow into discrete, visible colonies in the pattern in which they were inoculated.

When the colonies have grown, the Petri dish may be re-placed above the paper grid and portions of the colonies removed for screening. Typically this involves further growth ("subculturing") of the colony portion, followed by analysis. Those colonies having the desired characteristic(s) may be selected by reference back to the original colonies grown in the Petri dish. The dish may be replaced above the paper grid, with the reference mark on the Petri dish being aligned with that on the up-turned Petri dish lid, substantially to recreate the original spatial relationship therefore ensuring that the colonies on the Petri dish can be correctly identified with reference to the numbered grid. The Petri dish bearing discrete colonies set out in a matrix in this fashion is commonly termed the "master plate".

SUMMARY OF THE INVENTION

In a first aspect the invention provides a Petri dish support device comprising two opposed portions, and a space defined between said opposed portions capable of receiving a sheet of material having marked thereon a matrix, the support being adapted to secure a Petri dish above the marked matrix, the matrix being visible through the base of the Petri dish.

The opposed portions of the device are desirably movable between a closed, operable position and an open, adjustment position. Conveniently the opposed portions are attached by a hinge joint, which allows for relative axial movement of the portions about the hinge between the closed and open positions. The opposed portions conveniently comprise a synthetic plastics moulded material, such as ABS.

In the closed, operable position the opposed portions of the device preferably fit together substantially flush so as to form a housing and define a space capable of receiving a sheet of material having a matrix marked thereon, the housing substantially enclosing the matrix-bearing sheet of material. The matrix may be one of any of a number of such matrices commonly used by those skilled in the art. For example, the matrix may take the form of a plurality of squares, set out so as to fit within the diameter of a conventional 90 mm diameter Petri dish. The squares may be numbered (e.g. 1 to 25, 1 to 50, or 1 to 100) or blank. Alternatively, the matrix may be a circle divided into a number of sectors (e.g. 6 or 12). Typically the matrix will be marked on the sheet of material by printing or similar process.

The matrix-bearing sheet of material may conveniently be a synthetic laminate material, which may be opaque or transparent. The use of a transparent material (such as acrylic or acetate) allows for the device to be used with a light box or similar apparatus, such that Petri dishes placed on the support may be back-lit. Where the matrix-bearing sheet of material is opaque, the sheet may be reversible, having different matrices marked on respective faces.

It is preferred that the device is provided with a plurality of matrix-bearing sheets, typically with different sheets bearing different respective matrices thereby rendering the device more versatile. Conveniently, the plurality of matrix-bearing sheets are connected so as to form a single component locatable within the space defined between the opposed portions of the device. In one particular embodiment, a plurality of matrix-bearing sheets are connected by a ring binder, so as to form a small booklet of matrix-bearing sheets, each sheet having marked on a surface thereof a matrix.

It will be appreciated that where the device comprises a plurality of transparent matrix-bearing sheets, each sheet having a different matrix marked thereon, confusion can occur if the sheets are positioned beneath each other in use, as the matrices marked on lower sheets will be visible through the uppermost sheet of material. Accordingly, where a plurality of transparent matrix-bearing sheets are provided with the device, it is preferred that the sheets may be so arranged that when in use, the matrix marked on only a single sheet is visible in the region above which the Petri dish is positioned.

Conveniently, a separate opaque sheet of screening material is provided which may be located beneath the sheet bearing the desired matrix (which sheet is placed uppermost of the plurality of matrix-bearing sheets). The opaque screening sheet serves to prevent the appearance to a user of the undesired matrix-bearing sheets. Preferably the opaque screening sheet is of a suitable colour so as to provide contrast with the desired matrix marked on the transparent matrix-bearing sheet. Thus, for example, where the matrix is marked in black on a transparent sheet, the opaque screening sheet may be white, and vice versa.

If a different matrix is desired, the opposed portions are moved into the open, adjustment position. The appropriate matrix-bearing sheet is positioned uppermost in the device and the opaque screening sheet placed beneath, blocking the appearance of the undesired matrices.

It will be apparent to those skilled in the art that the use of a screening sheet of opaque material, as described above, will prevent the possibility of using a light-box or similar apparatus to cause back-lighting of the Petri dish (and any colonies growing therein) whilst supported on the device. Conveniently therefore in one embodiment, the device comprises a plurality of transparent matrix-bearing sheets forming a ring-bound booklet, and in the closed, operable position a slot is formed between the opposed portions. The sheet with the desired matrix may be positioned within the device so as to be visible beneath a supported Petri dish. The remaining matrix-bearing sheets in the booklet may be passed through the slot and out of the device, so as not to confuse a user. The device may then be placed on top of a light-box or similar apparatus, so as to cause back-lighting of the supported Petri dish.

Conveniently the interior faces of the opposed portions are so shaped as to accommodate a ring binder or similar connection means used to connect the plurality of matrix-bearing sheets. Further, the device is preferably provided with a retaining means to retain the plurality of matrix-bearing sheets in position. For example, the retaining means may take the form of a pair of projecting fingers formed on the interior surface of one of the opposed portions which are received within co-operating recesses formed on the interior surface of the other opposed portion. The matrix-bearing sheets may be punched with holes of suitable diameter, such that the projecting fingers may pass through the holes in the sheets and into the co-operating recesses, thereby retaining the sheets in position. Conveniently, where an opaque screening sheet is provided, the screening sheet may be retained by the same retaining means which serve to retain the matrix-bearing sheets. Alternatively, separate retaining means may be provided for the screening sheet.

In a preferred embodiment the opposed portions are substantially identical (with the exception of certain minor features, described below), such that the device is substantially reversible and may be used with either of the opposed portions uppermost. Advantageously each opposed portion is provided on its exterior face with projecting feet, which are preferably formed of, or coated with, a non-slip material. The feet protect the device from scratches and prevent movement in use. Desirably the feet are such that when the device is placed on a flat surface, such as a laboratory bench, the device rests at a small angle to the horizontal (about 10°), which is optimal for comfortable use and also tends to catch ambient light at an angle for improved visibility of colonies on a dish, or for the matrix beneath. Conveniently two pairs of feet are provided on each opposed portion, the respective pairs of feet typically being disposed towards opposite end regions of the device.

If desired, the feet on one portion may be of different length to those on the other portion, such that the device may be held at a different angle to the bench, depending on which portion of the device is lowermost.

The device is such that the matrix marked on the sheet of material is visible when the device is in use. The matrix may be visible because the opposed portions comprise cut-outs (typically circular). However, such cut-outs leave the matrix-bearing sheet exposed to possible damage (e.g. exposure to dangerous chemicals, or physical damage). Accordingly it is preferred that the opposed portions substantially enclose the displayed matrix-bearing sheet, but that the region overlaying the displayed matrix-bearing sheet is made of a transparent substance, such as polycarbonate.

The support device is desirably provided with Petri dish securing means, which conveniently comprises a resiliently deformable material which enters into frictional engagement with a Petri dish located on the support. In a preferred embodiment, the securing means comprises a nitrile or a silicon rubber O ring. Preferably the securing means also serves as a closure means to keep the opposed portions of the device in the closed position.

Thus in one embodiment the exterior surfaces of the opposed portions are formed with a groove therein. The groove accepts a nitrile or silicon rubber O ring, the tension in which is sufficient to keep together the portions of the device in the closed position. In addition the O ring may act as a Petri dish securing means. In use a Petri dish is positioned on the exterior surface of the uppermost portion of the device, the lowermost edge of the dish resting on the projecting feet. The uppermost edge of the Petri dish enters into frictional engagement with the silicon rubber O ring which stretches across the support device from side to side. This arrangement has the advantage that the Petri dish may be firmly secured on the support device, despite slight variations in dimension which are found in Petri dishes produced by different manufacturers.

If a different matrix is required to be displayed, the O ring can be removed from the groove, thus allowing the opposed portions to be moved into the open, adjustment position.

In a preferred embodiment the exterior surface of one or both opposed portions is provided with one or more reference marks, such as an arrow, which is conveniently formed by appropriate moulding of the opposed portions.

As an alternative closure means, the opposed portions may be provided with a snap-fit closure mechanism.

The invention will now be further described by way of illustrative example and with reference to the accompanying drawings, in which:

DESCRIPTION OF THE PREFERRED EMBODIMENT

Figure 1:
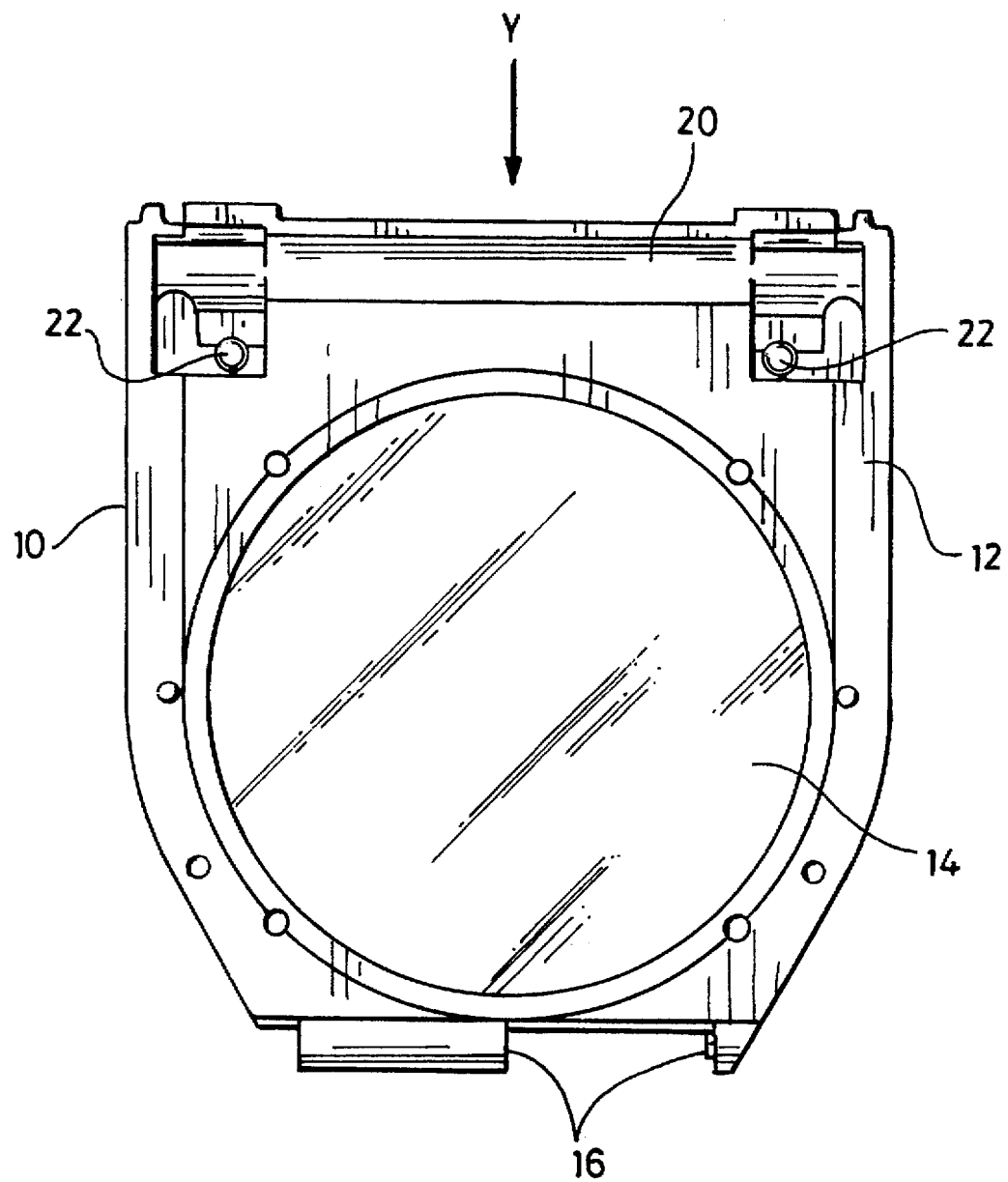
FIG. 1 shows in plan view the interior surface of a portion of a Petri dish support device in accordance with the invention.
Figure 2:
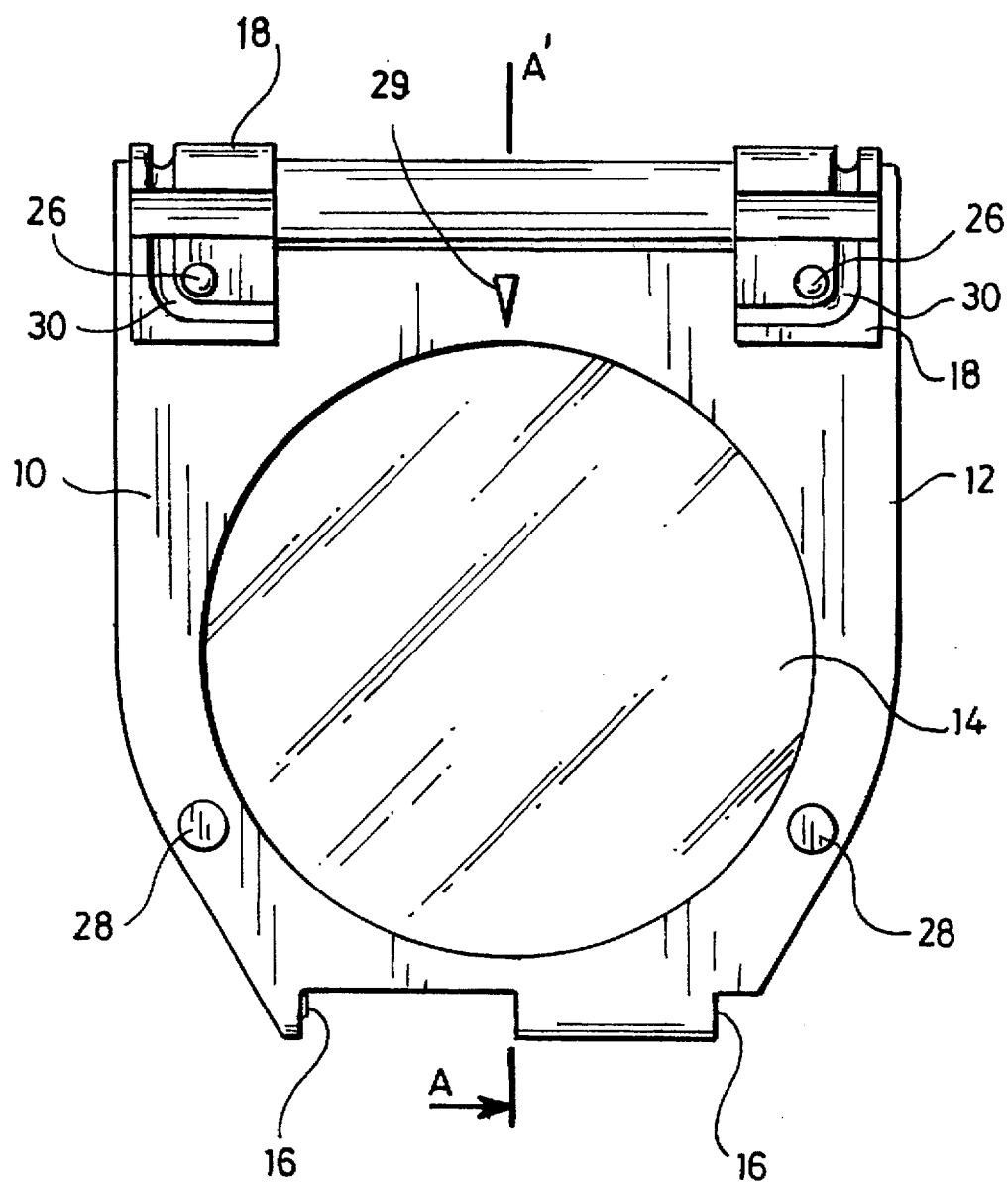
FIG. 2 shows in plan view the exterior surface of the portion shown in FIG. 1.

Referring to the Figures, a Petri dish support device comprises two opposed portions. FIG. 1 shows the interior face of one portion 10 in plan view, separated from its opposing portion. FIG. 2 shows the exterior face of the portion 10 in plan view, also separated from its opposing portion. The opposed portion of the device is not illustrated but is substantially identical in most respects. The portion 10 comprises an opaque outer region 12 of moulded synthetic plastics material (ABS) around an inner circular region 14 of transparent polycarbonate material. The inner region 14 has a diameter of about 82 mm (slightly less than that of a typical Petri dish). The outer region 12 has a length of about 115 mm, a width of about 104 mm, and a depth, for the most part, of about 4 mm.

The portion 10 may be attached to its opposed portion by a mutually engaging hinge attachment 16 at the lower edge of the opposing portions. The hinge attachment allows for the portion 10 and its opposing portion to be movable between an open, adjustment position and a closed, operable position, in which the opposed portions fit together substantially flush so as to form a housing and define a space capable of receiving a sheet of material having marked thereon a matrix, the matrix-bearing sheet being substantially enclosed within the housing formed by the opposing portions.

Figure 3:
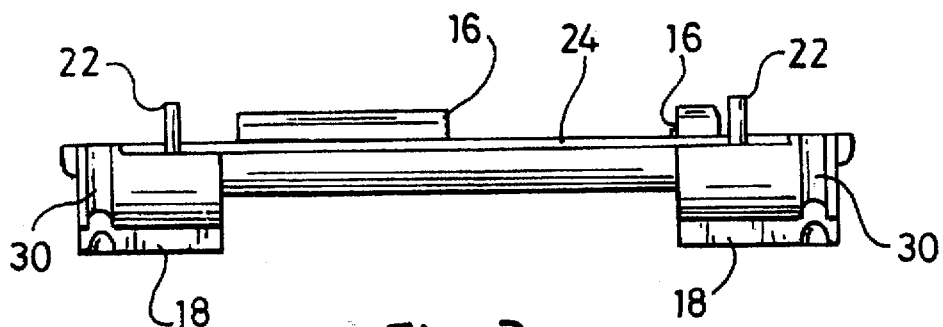
FIG. 3 shows an end elevation of the portion shown in FIG. 1, seen from the end marked "Y" in that Figure.
Figures 4, 5:
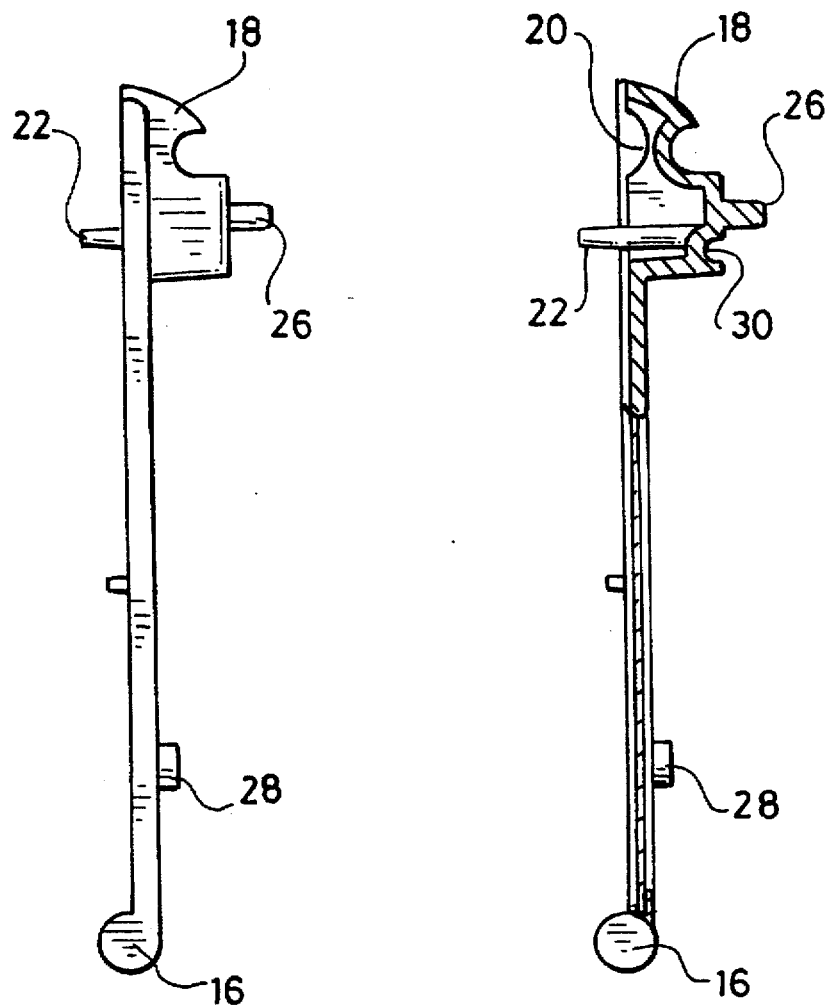
FIG. 4 is a side elevation of the portion shown in FIG. 1.
FIG. 5 is a sectional view of the portion, along the line A-A' shown in FIG. 2.

The portion 10 illustrated in the Figures is intended for use in a Petri dish support device which accommodates a booklet, the booklet comprising a plurality of transparent acetate sheets connected by a metallic ring binder, each sheet having marked on one face a respective matrix. At the top end of the portion 10 are two shoulders 18, best seen in the end elevation FIG. 3, the side elevation FIG. 4 or the sectional view FIG. 5. The shoulders 18 serve to raise the device above a work surface upon which the device may be placed (although it is preferred that the shoulders 18 do not directly contact the work surface, as explained below), and generally present the device at an angle thereto. The portion 10 and its opposed portion are shaped so as to accommodate the booklet. Accordingly between the shoulders 18 is a recess 20 which accommodates the ring binder of the booklet of matrix-bearing sheets.

The portion 10 is also provided with retaining means to retain the booklet in position. The retaining means comprises a pair of projecting fingers 22 located at the upper end of the interior face of the portion 10. The matrix-bearing sheets of acetate in the booklet are punched with corresponding holes, so that the booklet can be mounted on the projecting fingers 22. The interior face of the other portion of the device (not shown) is formed with co-operating recesses, which accommodate the fingers 22 when the opposed portions are in the closed, operable position.

The position of the fingers 22 and the holes in the acetate sheets is such that the matrix marked on a particular sheet is displayed to a user through the transparent inner region 14 of the portion 10, which region protects the displayed sheet from physical or chemical damage.

The matrix-bearing acetate sheets are transparent, so the device can be back-lit (for example, using a light-box). However, the presence of other transparent sheets with different matrices marked thereon, beneath the desired displayed sheet, would cause confusion as several matrices would be visible simultaneously. Accordingly, the device is provided with a separate opaque sheet of synthetic plastics material (not shown), which can be inserted between the displayed matrix-bearing sheet and the undesired matrix-bearing sheets, so as to prevent the appearance to a user of the undesired matrices. In addition, so that the device can be used with a light-box or similar apparatus, the portion 10 is provided at its upper end with a notch 24. A similar notch is provided at the upper end of the opposed portion. Accordingly, when the opposed portions are brought together into the closed, operable position a passage is formed between the two portions, which extends from the space defined between the interior faces of the opposed portions to the exterior of the device. Thus, whilst the opposed portions are in their open, adjustment position the desired acetate sheet in the booklet may be located so as to be within the space defined by the opposed portions when in their closed, operable position, and so displayed under the transparent inner region 14 of the portion 10. The other, undesired matrix-bearing sheets in the booklet may be folded over the ring binder so as to pass over the notch 24. When the opposed portions are brought into the closed, operable position, the undesired sheets fit within the passage formed between the respective upper ends of the opposed portions and pass out of the device, out of the line of sight of the user, who is free to concentrate on the displayed matrix.

Referring to FIG. 2, the exterior of the portion 10 is provided with a pair of projecting feet 26 at the upper end, which are formed on the shoulders 18. There are also a smaller pair of projecting feet 28 provided at the lower end of the exterior of the portion 10. These feet in use are covered with a non-slip material to protect the portion 10 from becoming scratched and to prevent movement of the device on the work surface, which might occur if the shoulders 18 directly contacted the work surface. The feet 28 project to a lesser extent than the feet 26 such that, when the device is placed on a horizontal surface, portion 10 lowermost, the device is held at a small angle (about 10°) to the horizontal, for comfortable use and to catch indcident light at an angle, for improved visualisation of microorganism colonies growing in a supported Petri dish and/or to facilitate visualisation of the matrix marked on a sheet of acetate within the device. An arrow head reference mark 29 is formed in the portion 10 which facilitates correct alignment of a Petri dish on the device. A similar reference mark is provided on the opposed portion (not shown) of the device.

The other portion of the device is similarly equipped with upper and lower end region feet. However, the difference in the length of projection between the upper and lower end region feet is less than in portion 10 illustrated in the Figures. Accordingly when the device is used with portion 10 uppermost, the angle of inclination to the horizontal is less (about 5°) than when the portion 10 is lowermost. The device thus provides for two different angles of presentation to the user, depending on its orientation.

The device is also provided with closure means, which comprises a silicon rubber O ring which passes, under tension, around the upper end of each of the opposed portions. The O ring is locatable within a groove 30 (shown in FIGS. 2 and 3) provided on the exterior face of the shoulders 18 each portion of the device. The groove 30 in portion 10 marries with the similar groove formed in the opposed portion, such that a continuous groove is formed across the two portions when they are brought into the closed, operable position. The O ring is readily removed from the groove 30 to allow a user to open the device by moving the opposed portions about the mutual hinge region.

The silicon rubber has an additional function, in that it also serves to secure firmly a Petri dish located on the support device, whilst still allowing for minor variation in dimensions which is encountered in Petri dishes produced by different manufacturers. A Petri dish to be supported by the device rests, at its lower edge, against the feet 28 at the lower end region of the portion 10 (or the corresponding lower end region feet provided on the opposed portion, depending on the orientation of the device). The Petri dish is firmly secured by passing the tensioned silicon rubber O ring across the upper edge of the Petri dish, thereby placing the dish in frictional engagement between the O ring and the lower end region feet 28.

We claim:

1. A Petri dish support device comprising two opposed portions, a space defined between said opposed portions, and a sheet of material having marked thereon a matrix, said sheet being located in the space defined between said opposed portions, the support device being adapted to secure a Petri dish above the marked matrix, the matrix being visible through the base of the Petri dish.

2. A device according to claim 1, wherein the opposed portions are substantially flush in their closed, operable position, so as to form a housing which essentially encloses the sheet of material displaying a desired matrix.

3. A device according to claim 1, wherein the opposed portions of the device are essentially identical.

4. A device according to claim 1, wherein the opposed portions comprise a transparent region, through which the matrix marked on the sheet of material is displayed.

5. A device according to claim 1, accommodating a plurality of sheets of transparent material, each sheet having a respective matrix marked thereon.

6. A device according to claim 5, wherein the plurality of sheets are connected by connecting means, so as to form a single component located within the space defined by the opposed portions.

7. A device according to claim 1, comprising retaining means to retain a sheet of material in the desired position.

8. A device according to claim 1, wherein the device is reversible such that in use either of the opposed portions may be uppermost.

9. A device according to claim 1, comprising projecting feet which hold the device at an angle when placed on a horizontal work surface.

10. A device according to claim 9, wherein the respective opposed portions present the device at a different angle when placed on a horizontal work surface.

11. A device according to claim 5, comprising means to prevent the appearance to a user of undesired matrices in the line of sight of a desired matrix.

12. A device according to claim 11, comprising an opaque sheet of screening material located beneath a desired matrix.

13. A device according to claim 1, comprising releasable closure means to hold the opposed portions in their closed, operable position.

14. A device according to claim 1, comprising securing means to secure firmly a Petri dish supported on the device.

15. A device according to claim 13, wherein the functions of the releasable closure means and the securing means are performed by the same component.

16. A device according to claim 14, wherein the functions of the releasable closure means and the securing means are performed by the same component.

17. A device according to claim 13, comprising an O ring.

18. A device according to claim 14, comprising an O ring.

19. A device according to claim 15, comprising an O ring.

20. A device according to claim 16, comprising an O ring.

* * * * *